United States Patent [19]

Kobayashi

[11] Patent Number: 5,090,044
[45] Date of Patent: Feb. 18, 1992

[54] X-RAY EXAMINATION APPARATUS

[75] Inventor: Tohru Kobayashi, Ootawara, Japan

[73] Assignee: Kabushiki Kaisha Toshiba, Kawasaki, Japan

[21] Appl. No.: 603,365

[22] Filed: Oct. 26, 1990

[30] Foreign Application Priority Data

Oct. 30, 1989 [JP] Japan .................................. 1-279873

[51] Int. Cl.[5] .............................................. G21K 1/00
[52] U.S. Cl. .................................... 378/145; 378/208; 378/209; 250/575.1
[58] Field of Search ............... 378/145, 204, 208, 209, 378/203; 250/505.1, 515.1, 517.1

[56] References Cited

U.S. PATENT DOCUMENTS

| 3,984,695 | 10/1976 | Collica et al. | 250/515.1 |
| 4,280,056 | 7/1981 | Renshaw | 250/515.1 |
| 4,581,538 | 4/1986 | Lenhart | 250/515.1 |
| 4,965,456 | 10/1990 | Huettenrauch et al. | 250/515.1 |

Primary Examiner—Janice A. Howell
Assistant Examiner—David P. Porta
Attorney, Agent, or Firm—Oblon, Spivak, McClelland, Maier & Neustadt

[57] ABSTRACT

For performing an X-ray examination wherein a catheter is inserted into a blood vessel of a subject from the brachial region, an X-ray shield is mounted on an arm rest to shield scattered X-rays passed from the subject, to thereby protect operator's hands handling the catheter.

13 Claims, 4 Drawing Sheets

X-RAY EXAMINATION APPARATUS

BACKGROUND OF THE INVENTION

1. Field of the Invention

This invention relates to an X-ray examination apparatus and more particularly, to an X-ray examination apparatus for examining the circulatory system, such as, the blood vessels and the heart.

2. Description of the Related Art

X-ray examination of the circulatory system is broadly classified into two methods. One method is angiocardiography in which blood flow, the running and form of the blood vessels, the movement of the heart, etc. is X-rayed by injecting a contrast medium of a high X-ray absorption property into the heart or blood vessel. The other one is cardio catheterization in which the circulation of blood or the cardiac function is examined by inserting a catheter into the heart or blood vessel and blood pressure or the rate of blood flow is quantitatively measured.

In both of these examination methods, a catheter is inserted into a blood vessel from the brachial or femoral region of a subject to be examined. The method of inserting a catheter from the brachial region is called the Sones method and the method of insertion from the femoral region is called the Judkins method. In performing an X-ray examination by inserting a catheter into the brachium of the subject, an arm is placed on an arm rest and insertion of the catheter takes place under X-ray fluoroscopy. Therefore, it is necessary to protect the operator handling the catheter against scattered X-rays.

X-ray protection gloves and protection aprons, for example, are available as means for protecting the catheter-handling operator against scattered X-rays. There exist difficulties, however, with the protecting gloves in that a fine touch in operating the catheter is not fully conveyed to the operator.

SUMMARY OF THE INVENTION

An object of this invention is to provide an X-ray examination apparatus capable of protecting the operator's arms/hands against scattered X-rays during catheterization by inserting a catheter into a blood vessel of the subject from the brachial region.

To accomplish the above object, the invention provides an X-ray examination apparatus which comprises a bed having arm rest means for supporting a brachial region of a subject when an operator inserts a catheter into a blood vessel of the subject from the brachial region; means for radiating X-rays to the subject lying on the bed; means for converting X-rays passing through the subject into an X-ray image; X-ray shield means, mounted on the arm rest means, for protecting arms/hands of the operator against scattered X-rays.

DETAILED DESCRIPTION OF THE PREFERRED EMBODIMENT

Figure 1:
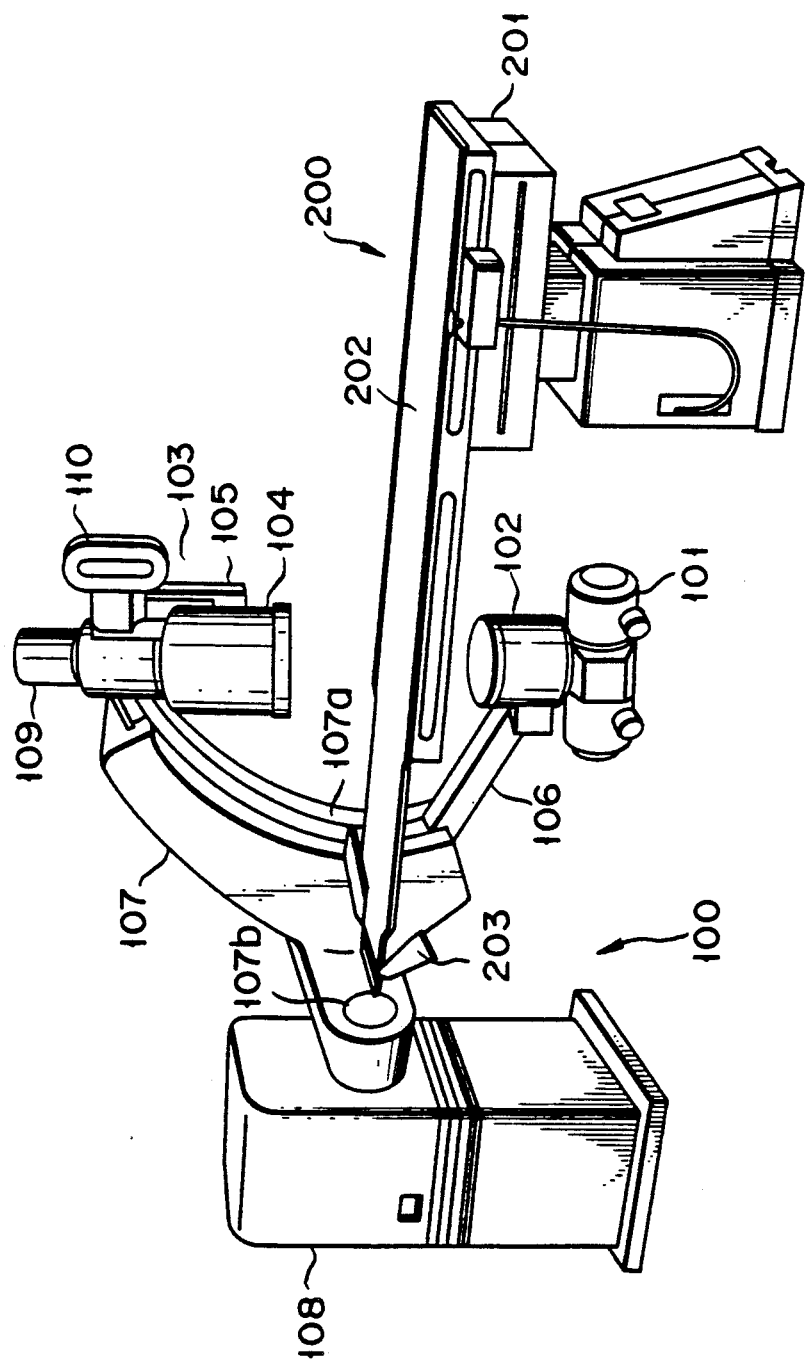
FIG. 1 shows a structural arrangement of an X-ray examination apparatus embodying this invention.

Reference will now be made in detail to the presently preferred embodiment of the invention as illustrated in the accompanying drawings, in which like reference characters designate like or corresponding parts throughout the several drawings.

One embodiment of the invention will be described with reference to the accompanying drawings.

As illustrated in FIG. 1, an X-ray examination apparatus embodying the invention comprises an X-ray imaging device 100 and a bed 200 provided in the vicinity of the X-ray imaging device 100.

Figure 3:
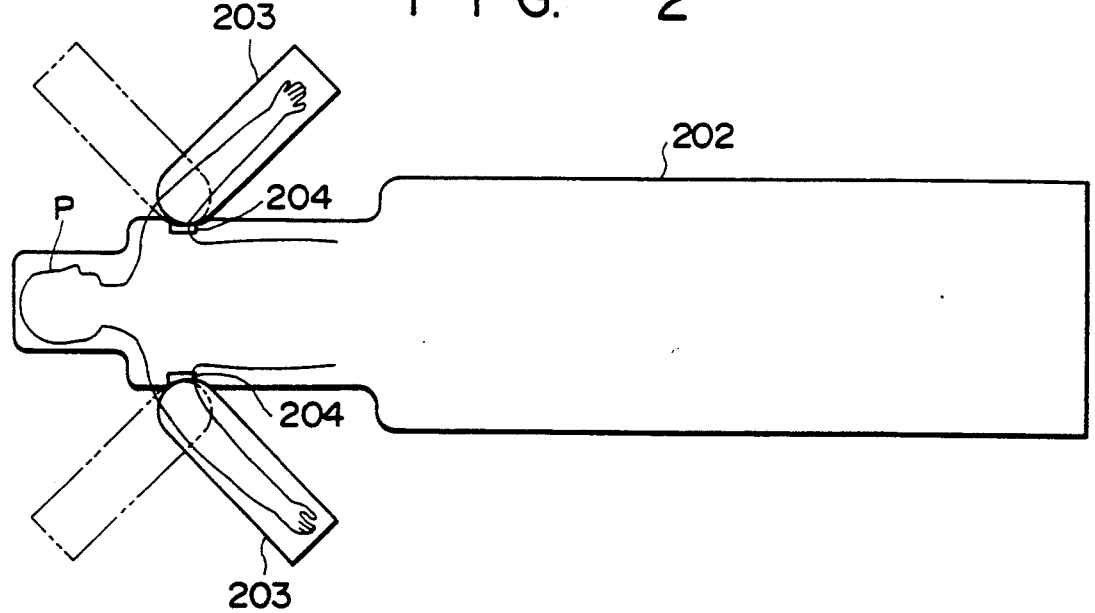
FIG. 3 is a plan view of a slidable plate mounted on the bed shown in FIG. 2.

The X-ray imaging device 100 comprises an X-ray radiation means 101 for radiating X-rays to a subject P (see FIG. 3) lying on the bed 200 and an X-ray image receiving means 103 for receiving X-rays penetrating the subject P. The X-ray radiation means 101 comprises an X-ray tube 102 for generating X rays and a movable X-ray iris, not shown, for adjusting an expansion of X-rays emitted by the X-ray tube 102.

The X-ray image receiving means 103 has functions to have an X-ray penetration image converted into a visible image by an image intensifier 104, have the visible image imaged by a TV camera 109 for output to a monitor TV, or to have the visible image recorded on cine films by a cine camera 110. The X-ray image receiving means 103 has a film changer 105 for recording an X-ray penetration image from the subject P on X-ray sensitive films. The image intensifier 104 and the film changer 105 are selectively used.

The X-ray radiation means 101 and the X-ray image receiving means 103 are held at both ends of a support arm 106 of substantially a letter C-shaped configuration. The support arm 106 is held in a guide groove formed in a spherical surface 107a of an arm guide 107 and movable in a circumferential direction of the spherical surface 107a.

The arm guide 107 is rotatably secured on a side surface of a vertical support post 108 via a rotary shaft 107b. The vertical support post 108 is vertically set on the floor.

Figure 2:
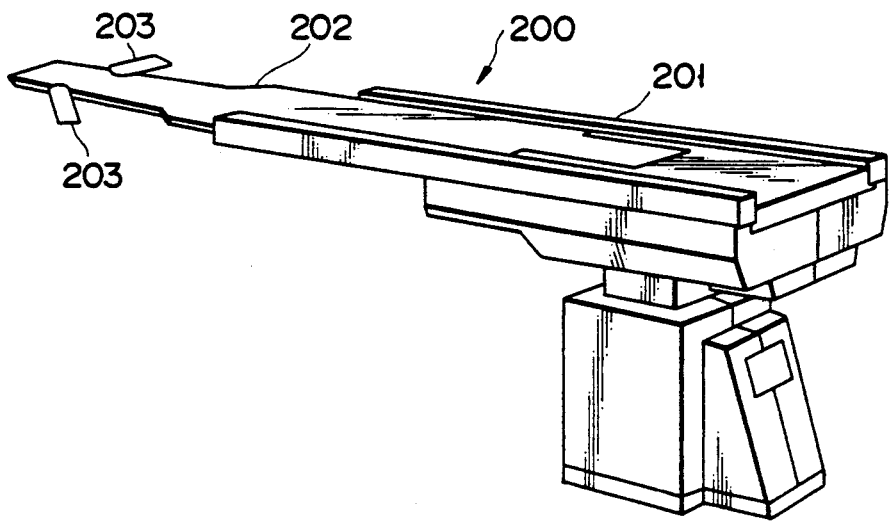
FIG. 2 is a perspective view of a bed used in the apparatus shown in FIG. 1.
Figure 4:
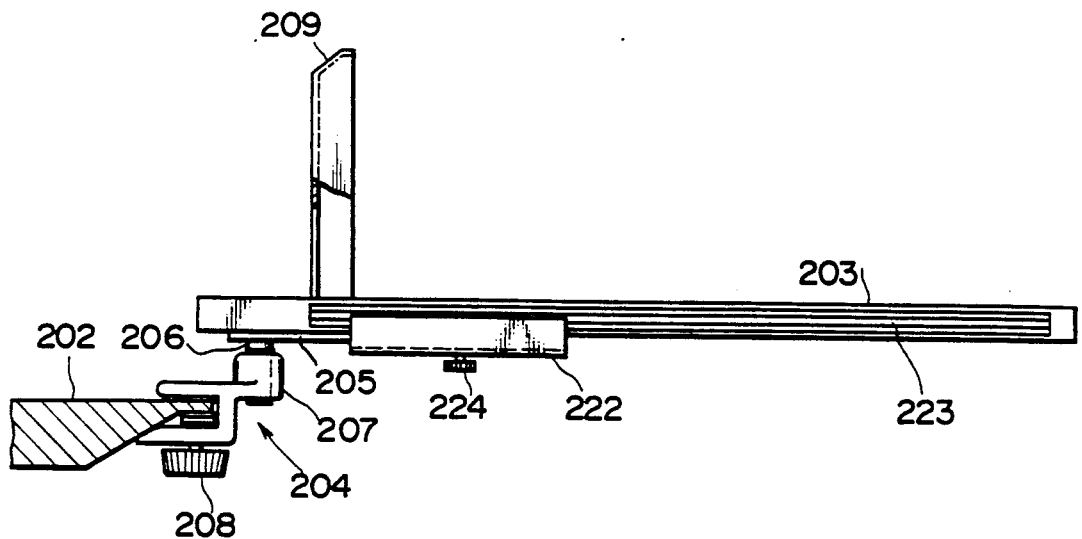
FIG. 4 is a side view of an arm rest provided on one side of the plate shown in FIG. 3.
Figure 5:
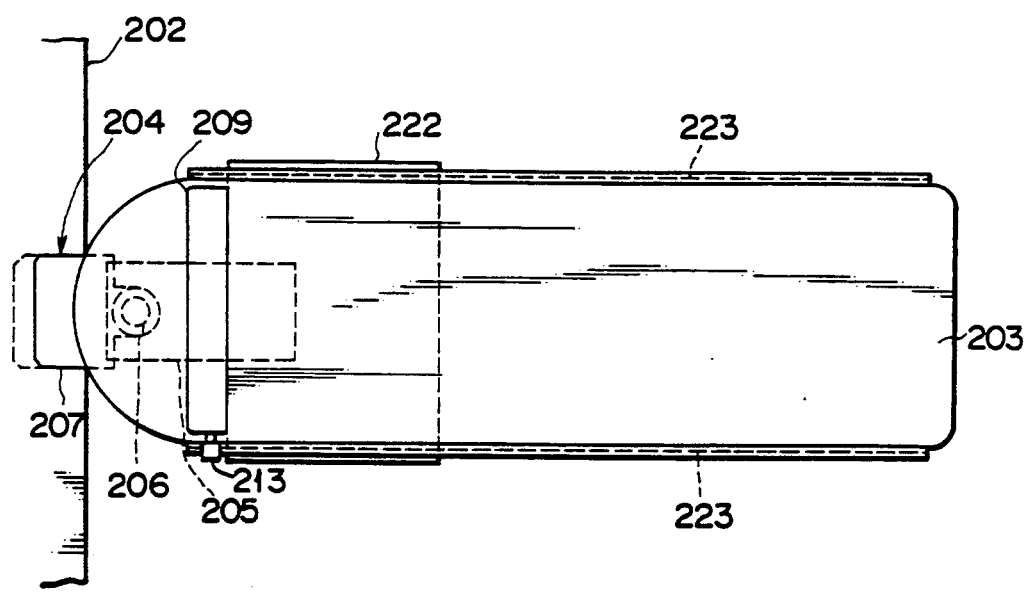
FIG. 5 is a plan view of the arm rest shown in FIG. 4.

As shown in FIG. 2, the bed 200 includes a bed body 201 placed on the floor of the examination site and a slidable plate 202 mounted on the bed body 201 and which is slidable in the longitudinal direction thereof. The bed 200 has two arm rests 203 for supporting arms of the subject P when an operator inserts a catheter into a blood vessel of the subject P from the brachial region. The arm rests 203 are connected to both sides of the slidable plate 202, and are rotatable in a horizontal direction and removable by means of connector units 204. The connector unit 204 is, as shown in FIGS. 4 and 5, formed, for example, of a fixing plate 205 secured on the bottom surface of the arm rest 203, a shaft 206 vertically suspending from the bottom surface of the fixing plate 205, a metal member 207 for rotatably supporting the shaft 206, and a fixing screw 208 for fixedly securing the metal member 207 on the slidable plate 202 at each side thereof.

Figure 6:
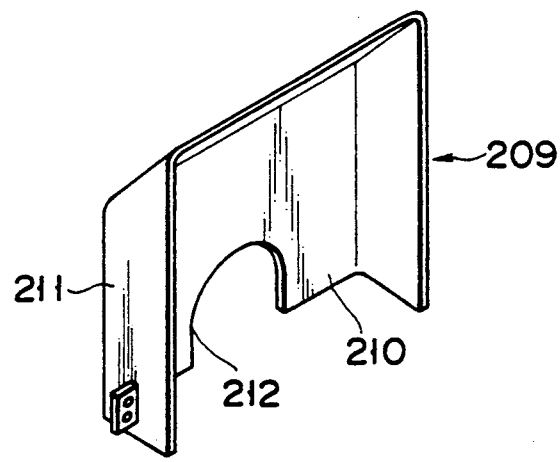
FIG. 6 is a perspective view of an X-ray shield mounted on the arm rest.
Figure 7:
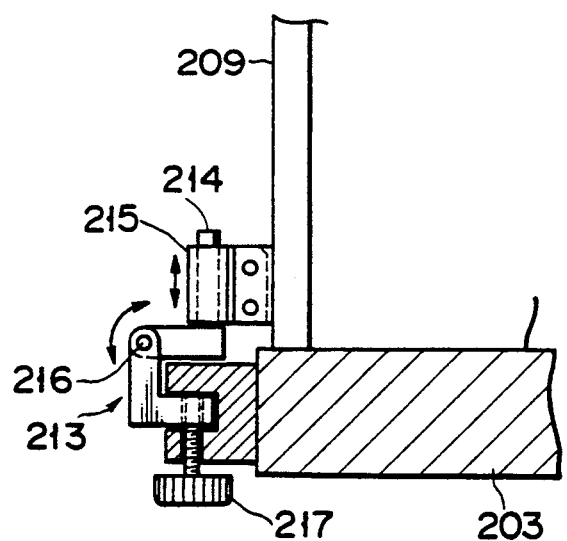
FIG. 7 is a view illustrating a mounting member for securing the X-ray shield to the arm rest.
Figure 8:
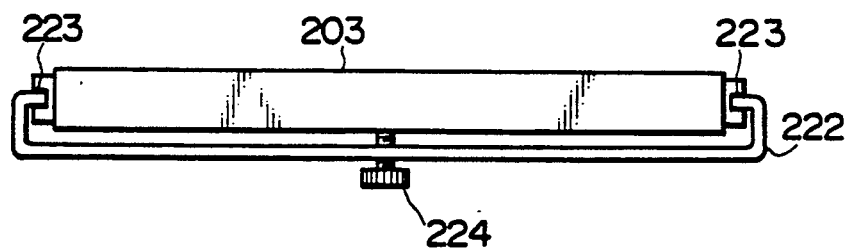
FIG. 8 is a view illustrating a cover for covering a bottom surface of the arm rest.

On each arm rest 203 is mounted, at a position closer to its pivotal end, an X-ray shield 209 for protecting the operator's hands/arms to shield scattered X-rays reflected from the surface of the body of the subject P. The X-ray shield 209 is formed of an X-ray shielding material, such as, lead-containing acrylic resin. As best illustrated in FIG. 6, the shield 209 includes a front wall 210 mounted on the arm rest 203 with its front surface directed to the carcass of the subject P, and edge walls 211 connected to all sides of the front wall 210 (except for the bottom side) and which extend towards the remote end of the arm rest 203, so that the hands and arms of the operator handling a catheter may be surrounded and shielded by the front wall 210 and the edge walls 211 from exposure to scattered X-rays reflected from the subject P. The front wall 210 has an opening 212 in the central bottom portion to permit the subject's arm to be passed therethrough. Further, the X-ray shield 209 preferably has approximately the same width as the arm rest 203 and a height equal to or greater than the thickness of the body of the subject P.

The arm rest 203 has a supporting unit 213 for supporting the X-ray shield 209 at one side of it. The supporting unit 213 includes a substantially vertically extending support pin 214 which is secured at one side of the X-ray shield 209 to removably support a hollow cylindrical member 215. The supporting unit 213 has hinge means 216 for moving the X-ray shield 209 from the arm rest 203 sidewardly thereof. The supporting unit 213 is secured to one side of the arm rest 203 by a fixing screw 217.

The arm rest 203 is provided with guide grooves 223 at its both side faces. The guide grooves 223 receive a cover plate 222 for covering a bottom surface of the arm rest 203, the cover plate 222 being slidable in the longitudinal direction of the arm rest 203.

The cover plate 222 is formed of the same X-ray shielding material as the shield 209, such as lead-containing acrylic resin, for shielding scattered X-rays reflected for example from the floor surface. The cover 222 is provided with a fixing screw 224 at its bottom central portion, which fastens the cover 222 to the arm rest 203 at a desired longitudinal position. The length of the cover 222 may for example be 20 to 30 cm when the length of the arm rest 203 is 60 to 70 cm.

By the above arrangement of the various component members, the operator's hands may be protected from exposure to scattered X-rays at the time of inserting a caterter into the blood vessel of the subject P from the brachial region. This may decrease dosage rate applicable to the operator. In addition, since the operator need not wear X-ray protection gloves, a fine touch may be easily conveyed onto the operator's hands.

According to the foregoing embodiment, the cover plate 222 is mounted on the arm rest 203 so as to be slidable in the longitudinal direction, so that X-ray fluoroscopy in the area of insertion of a catheter may be performed by rearwardly moving the cover plate 222. Further, according to the embodiment, the shield 209 which is removable from the arm rest 203 and movable from the upper surface of the arm rest 203 sidewardly of the arm rest 203 is not an obstacle to placing the arm on the arm reset 203.

Additional embodiments of the present invention will be apparent to those skilled in the art from consideration of the specification and practice of the present invention disclosed herein. It is intended that the specification and examples be considered as exemplary only with the true scope of the present invention being indicated by the following claims.

What is claimed is:

1. An X-ray examination apparatus comprising:
   a bed;
   means for radiating X-rays to a patient lying on the bed;
   means for converting the X-rays radiated to the patient into an image;
   an arm rest, connected to one side of the bed, for platforming an arm of the patient thereon when a catheter is inserted into a blood vessel of the patient from the arm; and
   X-ray shield means, mounted on the arm rest, for shielding scattered X-rays to protect arms/hands of an operator handling the catheter, the X-ray shield means having a front wall facing a carcass of the patient, edge walls disposed at sides of the front wall in a manner to surround the operator's hands, and an opening formed in the front wall to platform the patient's arm on the arm rest.

2. The X-ray examination apparatus according to claim 1, wherein the arm rest comprises means for removably supporting the X-ray shield means.

3. The X-ray examination apparatus according to claim 2, wherein the removable supporting means includes hinge means for moving the shielding means from an upper surface of the arm rest sidewardly of the arm rest.

4. The X-ray examination apparatus according to claim 1, wherein the X-ray shield means is formed of an X-ray shielding material.

5. The X-ray examination apparatus according to claim 1, wherein the front wall has a height equal to or greater than a thickness of a body of the patient.

6. The X-ray examination apparatus according to claim 1, wherein the front wall has approximately the same width as the arm rest.

7. An X-ray examination apparatus comprising:
   a bed;
   means for radiating X-rays to a patient lying on the bed;
   means for converting the X-rays radiated to the patient into an image;
   an arm rest, connected to one side of the bed, for platforming an arm of the patient thereon when a catheter is inserted into a blood vessel of the patient from the arm;
   X-ray shield means, mounted on the arm rest, for shielding scattered X-rays to protect arms/hand of an operator handling the catheter, the X-ray shield means having a front wall facing a carcass of the patient, edge walls disposed at sides of the front wall in a manner to surround the operator's hands, and an opening formed in the front wall to platform the patient's arm on the arm rest; and
   a cover, formed of an X-ray shielding material, for covering a bottom surface of the arm rest.

8. The X-ray examination apparatus according to claim 7, wherein the arm rest comprises means for slidably supporting the cover in a longitudinal direction of the arm rest.

9. The X-ray examination apparatus according to claim 8, wherein the slidably supporting means includes guide grooves formed in both side faces of the arm rest.

10. The X-ray examination apparatus according to claim 7, wherein the cover has a length which is equal to ⅓ to ½ the length of the arm rest.

11. The X-ray examination apparatus according to claim 7, wherein the cover comprises means for fixing itself to the arm rest at a desired longitudinal position.

12. The X-ray examination apparatus according to claim 11, wherein the fixing means includes a fixing screw which holds the cover in a static state to touch the bottom surface of the arm rest.

13. An X-ray examination apparatus comprising:

a bed;

means for radiating X-rays to a patient lying on the bed;

means for converting the X-rays radiated to the patient into an image;

an arm rest, connected to one side of the bed, for platforming an arm of the patient when a catheter is inserted into a blood vessel of the patient from the arm; and means for covering a bottom surface of the arm rest, formed of an X-ray shielding material.

* * * * *